Figures 2A, 2B:
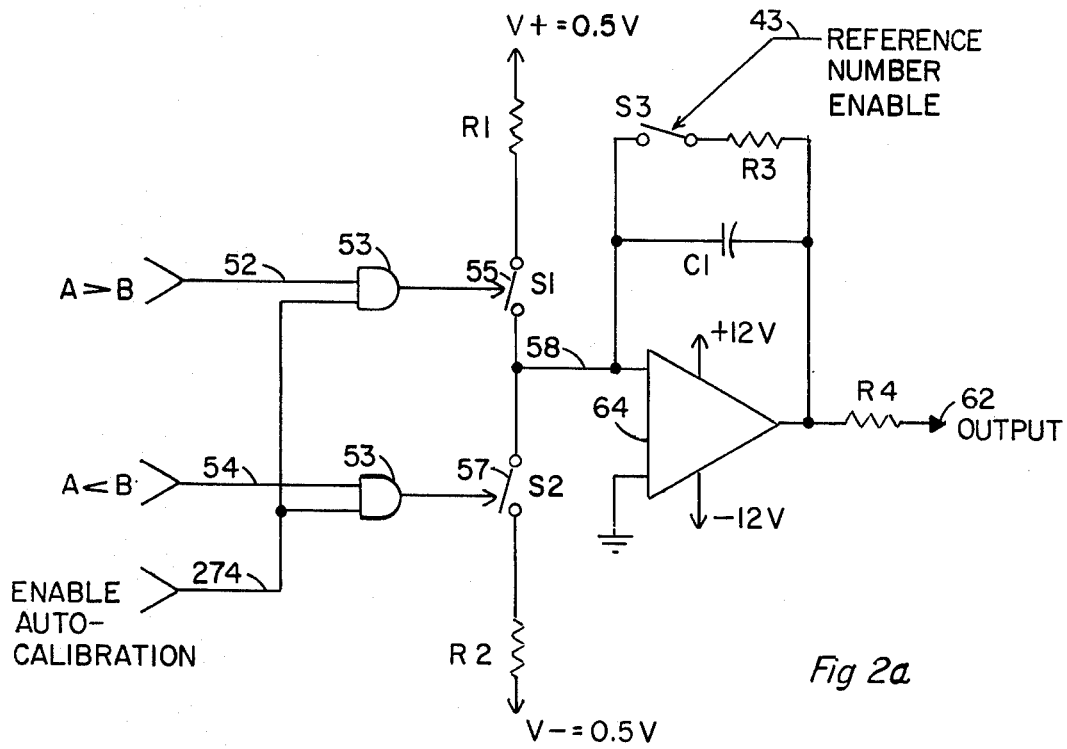

United States Patent [19]

Moran

[11] 4,039,933
[45] Aug. 2, 1977

[54] CONTINUOUS CALIBRATION SYSTEM AND METHOD FOR ANALYTICAL INSTRUMENTS

[75] Inventor: Byron L. Moran, Bedford, Mass.

[73] Assignee: Instrumentation Laboratory, Inc., Lexington, Mass.

[21] Appl. No.: 670,184

[22] Filed: Mar. 25, 1976

[51] Int. Cl.² .......................................... G01N 27/42
[52] U.S. Cl. ................................... 324/29; 324/30 R
[58] Field of Search .................... 324/29, 30 R, 78 E, 324/120, 130

[56] References Cited

U.S. PATENT DOCUMENTS

| | | | |
|---|---|---|---|
| 3,095,535 | 6/1963 | Jaffe et al. | 324/30 R |
| 3,781,677 | 12/1973 | Hagen | 324/78 E |
| 3,889,255 | 6/1975 | Pettersen | 324/30 R |
| 3,934,197 | 1/1976 | Pettersen | 324/30 R |

*Primary Examiner*—M. Tokar
*Attorney, Agent, or Firm*—G. Eugene Dacey

[57] ABSTRACT

A continuous automatic calibration system and fault detection method for analytical instruments of the kind used for measuring constituents of a fluid sample which system includes a memory for storing reference information, a comparator circuit for continuously comparing the instrument output to the stored reference information, and a sample-and-hold circuit charged positive or negative by the comparator, depending whether or not the instrument output exceeds the value of the reference information. The output of the sample-and-hold circuit in turn is coupled to the instrument continuously to adjust its output to correct value. Where the maximum allowed corrective range of the sample-and-hold circuit is exceeded by the signal from the comparator circuit beyond a predetermined time period, the system displays fault, warning the operator.

13 Claims, 4 Drawing Figures

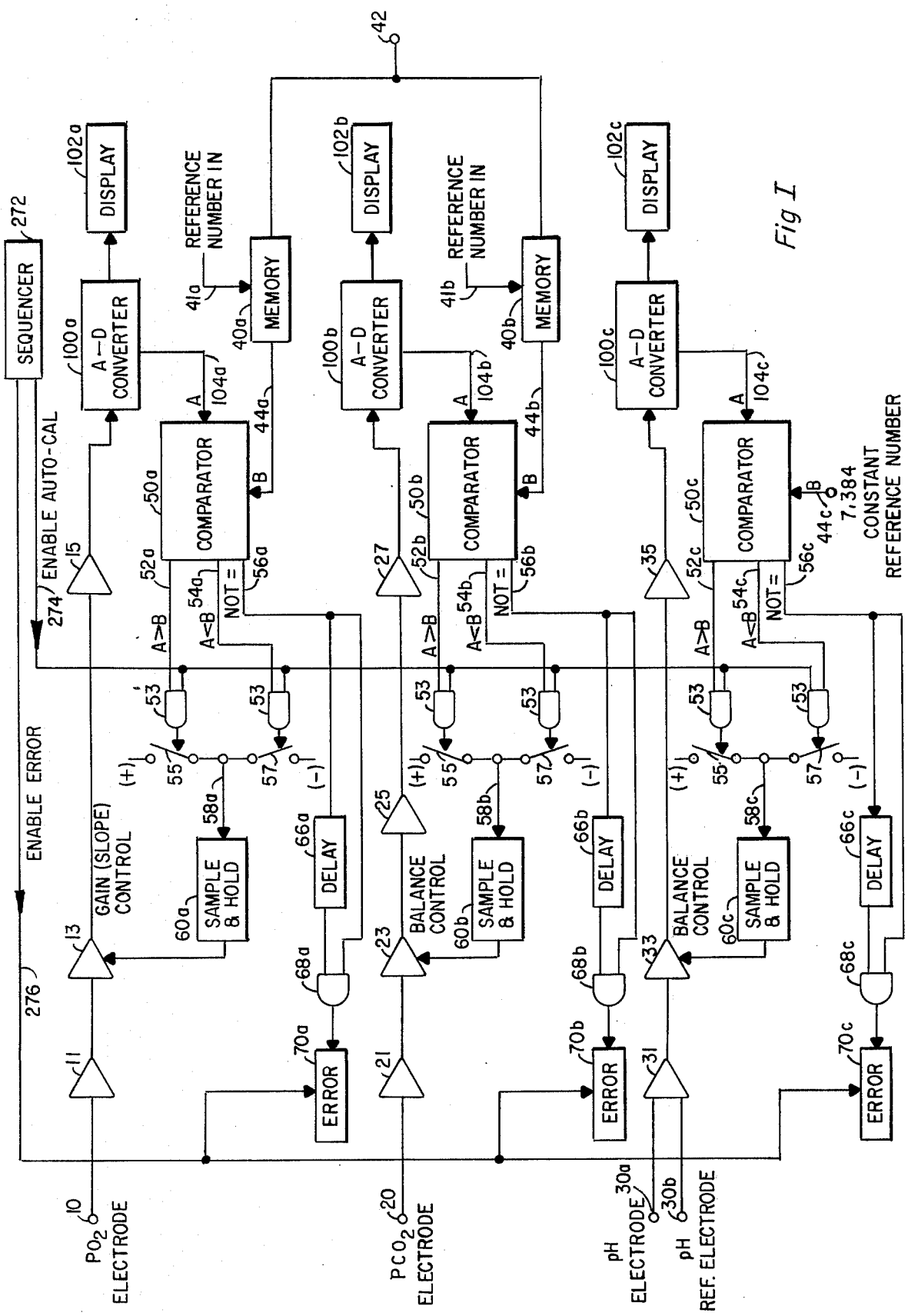
Fig I

| | R1 | R2 | R3 | R4 | C1 |
|---|---|---|---|---|---|
| pH | 1 MΩ | 1 MΩ | 10 KΩ | 2.7 MΩ | 2 µf |
| $Pco_2$ | 1.8 MΩ | 1.8 MΩ | 10 KΩ | 275 MΩ | 2 µf |
| $Po_2$ | 22 MΩ | 22 MΩ | 10 KΩ | 10 KΩ | 2 µf |

CONTINUOUS CALIBRATION SYSTEM AND METHOD FOR ANALYTICAL INSTRUMENTS

SUMMARY OF INVENTION

This invention relates to an analytical instrument and more particularly to an automatic continuous calibration system and fault detection method for use in such instruments. Such instruments are well-known for the anlaysis of parameters of precious fluids such as blood and also for parameters of constituents of our environment, whether it be in the streets, in a coal mine, on a submarine or the like.

Such analytical instruments include sensor means which are and of necessity have to be extremely sensitive to detect even the smallest required quantity of constituents in the fluid under investigation. Therefore, they must be precisely calibrated so as to give true and accurate readings of these constituents. This is particularly true since such information is frequently required for diagnostic purposes or in controlling life support means in the critically injured.

One kind of such an analytical instrument for the measurement of gaseous constituents of a sample of blood is described in detail in U.S. Pat. No. 3,672,843 entitled "Fluid Analyzing Apparatus," filed in the name of Thomas A. Rosse et al. and assigned to the same assignee as this application and, also in U.S. Pat. No. 3,694,734 entitled "Sensor Instrumentation," filed in the name of David E. Blackmer and assigned to the same assignee as this application. The disclosures of these two patents are incorporated herein by reference and, as will be more fully described below, the system of the present invention is fully compatible with and connectable to the apparatus disclosed in these patents.

In addition to an extremely sensitive sensor, some of which may be covered by a selectively permeable membrane depending upon the particular constituent to be analyzed, such analytical instruments include circuitry for producing an electrical signal that is representative of the particular constituent sensed by the sensor and also include an analog-to-digital converter to allow the ready display of such signal in easily readable digital form so as to be immediately available to an attending physician.

Because of the requirements for speed and accuracy in having such diagnostic information, it is most desirable, if not required, to have such analytical instruments in perfect calibrating condition immediately before a sample is presented to the instrument for analysis. Presently most analytical instruments do, of course, include calibration techniques which may vary from a manually adjustable calibration system as disclosed in the above mentioned U.S. Pat. Nos. 3,672,843; 3,694,734 to more automatic systems which include techniques which periodically and automatically calibrate such instruments in certain time intervals, say 30 minutes to 2 hours or that calibrate them on command by the operator.

Since the ideal situation is to have such an instrument constantly maintained in "stat" condition so that a sample may be presented to it almost at any time without requiring the operator to consider whether or not the instrument is properly calibrated, it is most desirable to have a system that so maintains such analytical instruments in perfect calibration at all times, automatically and without operator intervention. Operator intervention need only be required where the continuous calibration system is unable for one reason or another to calibrate the instrument. In that case, the instrument is preferably rendered inoperative so as to warn the operator that his intervention is required before the presentation of the sample.

Accordingly, it is an object of this invention to provide a continuous automatic calibration system and fault detection method for analytical instruments of the kind used for measuring constituents of a fluid sample. More specifically, it is an object of this invention to provide a continuous automatic calibration system and fault detection method which is capable to correct for certain slow response characteristics inherent in such instruments, to correct for minor system noises and shifts in readings occasioned by small variations in either the sensor, the circuitry or the readout means and, which will indicate instrument malfunction where it cannot correct the errors so as to warn the operator, requiring his intervention.

In accordance with a feature of the invention, there is provided a continuous automatic calibration system for analytical instruments which includes at least one sensor means in communication with a sample introduced into a suitable chamber, circuitry for producing a signal representative of the constituent sensed by the sensor and including an analog-to-digital converter to allow for display of the signal in digital form. Such a continuous automatic calibration system includes a memory means designed to receive and store reference information which is constantly compared by a comparator circuit with the instrument's output and produces a signal representative of any difference between the instrument's output and the reference signal. Associated with the comparator circuit is a sample-and-hold circuit designed to receive from the comparator circuit the signal representing the difference between instrument output and the reference information and which in response thereto produces a compensatory voltage at its output designed to be coupled to the circuitry of the analytical instrument so as to correct for errors in its readout system.

Should the above described continuous automatic calibration system not be able to correct for errors in the readout of the analytical instrument within a given period of time, either because it represents a major system breakdown or is beyond the capability of the system to correct, then a suitable error display means is provided, also receiving a signal from the comparator circuit. This error display means will inhibit use of the analytical instrument and will warn the operator by some suitable means, such as flashing display, that his intervention in correcting the instrument is required before sampling.

Thus, the present invention provides a simple, relatively inexpensive means for continuously and automatically calibrating analytical instruments and for indicating instrument malfunctions without any further specific circuitry. The result is the availability of such analytical instruments in stat condition ready to receive samples to be analyzed to operating personnel at all times.

Other objects, features and advantages of the invention may become more fully apparent from the following detailed description of a particular embodiment, taken together with the accompanying drawings, in which:

FIG. 1 is a block diagram of a continuous automatic calibration system as it may be incorporated in and applied to a specific blood gas instrument for measuring pH, PCO$_2$ and PO$_2$ values of blood specimens.

Figure 3:
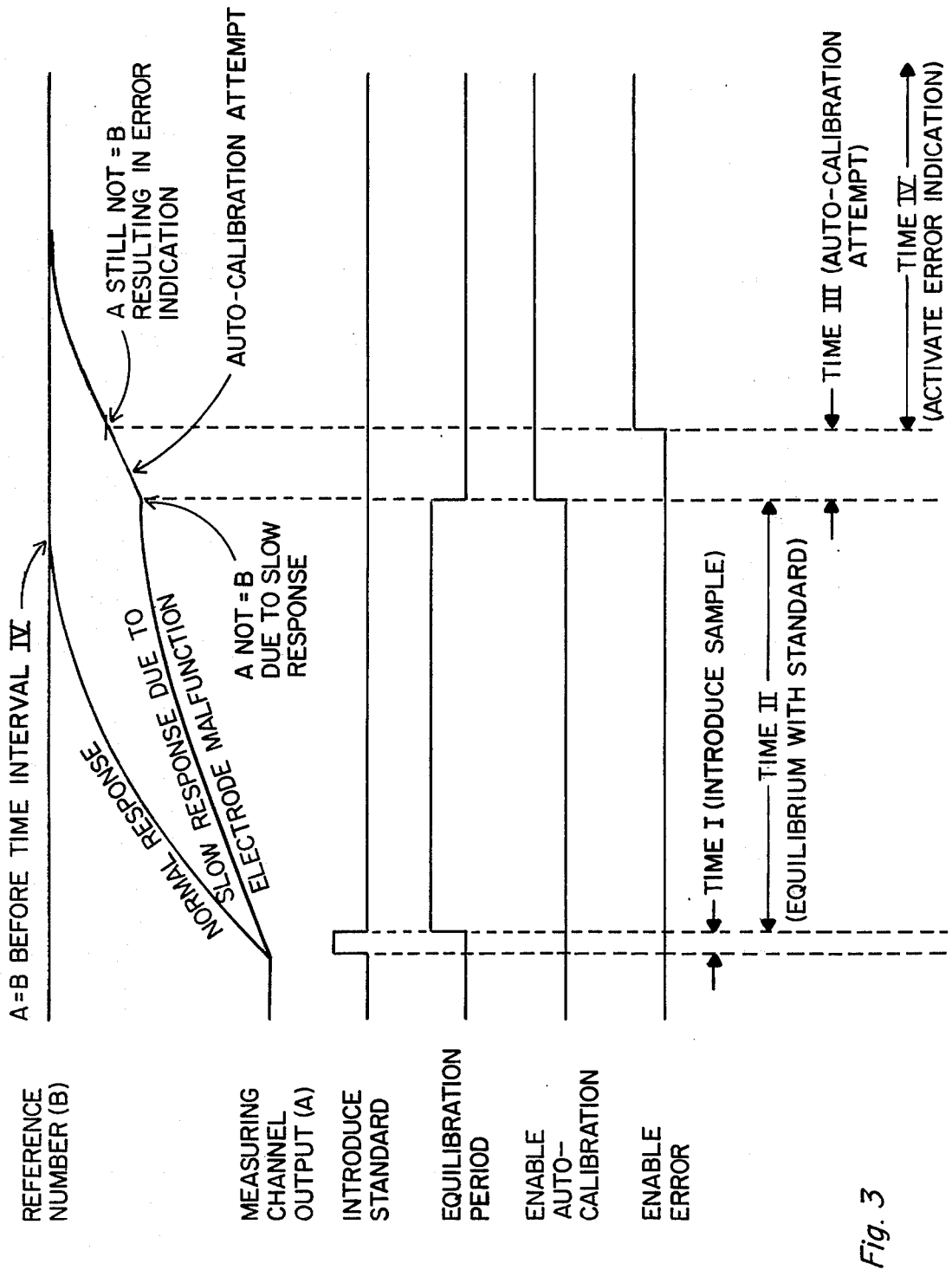

FIG. 2a is a schematic diagram of the sample-and-hold circuit shown in FIG. 1, and showing the same in more detail, FIG. 2b is a table giving the various representative values for the operative components of the sample-and-hold circuit, depending whether the same is used in the pH or the PC$_2$ or the PO$_2$ channel, and FIG. 3 depicts the timing diagram for the continuous automatic calibration system of the invention.

DESCRIPTION OF PARTICULAR EMBODIMENT

With reference to FIG. 1, there is shown in block diagram a particular embodiment of the continuous automatic calibration system of the invention as it has been incorporated into a specific blood gas instrument made by the assignee of this application and, as more specifically shown and described in U.S. Pat. No. 3,672,843. This particular blood gas instrument is a three channel analytical instrument designed to measure the pH, PCO$_2$ and PO$_2$ values of whole blood.

Basically, such an instrument includes a PO$_2$ electrode 10 which forms the sensor means for measuring the partial pressure of oxygen in the blood and is associated with circuitry such as amplifiers 11, 13, and 15 designed to produce a signal representative of such partial pressure of oxygen and also includes an analog-to-digital converter 100a so that the signal may be converted to digital form to be displayed for easy reading on a suitable display means 102a. The second channel includes a PCO$_2$ electrode 20 which may be identical to the electrode assembly having the same reference numeral and described in U.S. Pat. No. 3,694,734, note particularly FIG. 1 thereof. Of course, each such electrode assembly is associated with a sample chamber into which the specimen is introduced, as more fully disclosed in said U.S. Pat. Nos. 3,694,734 and 3,672,843. This PCO$_2$ channel 20 is also associated with its circuitry, including amplifiers 21, 23, 27, and also an anti-log circuit 25 and, also including its analog-to-digital converter 100b and digital display means 102b.

The pH sensor means, as is well-known and disclosed in our said U.S. Pat. No. 3,762,843, basically comprises a pH measuring electrode 30a and a pH reference electrode 30b which are disposed in a suitable junction assembly (not shown), such as may be disclosed in said U.S. Pat. No. 3,762,843. This pH sensor means also has its associated circuitry, including amplifiers 31, 33, 35 and analog-to-digital converter 100c and its digital display means 102c.

What has so far been described represents of course the essential and basic elements of a three-channel blood gas analyzer instrument. The continuous automatic calibration system of my invention will have to be coupled to each of these three-channels, as now more fully described.

The continuous automatic calibration system of my invention includes a memory circuit 40a, 40b which may be a 12-bit latch circuit. This memory circuit is designed for receiving and storing a reference number which has to be manually dialed in through signal paths 41a and 41b. It should be noted that the pH channel does not require such a memory circuit since for the purpose of calibrating this channel, the high buffer solution value of 7.834 is used as the constant reference number.

In the blood gas instrument provided with my continuous automatic calibration system, it is required that standard calibration gases and a pH buffer solution are constantly maintained in the respective measuring chambers except of course when a sample is being analyzed and also following such analysis when the measuring chambers and associated tubes are flushed and cleaned by a flushing solution. Hence to activate the continuous automatic calibration system of my invention, the operator first introduces, via signal paths 41a and 41b, the reference numbers of the standards which are known to him and are in the respective measuring chambers, into the memory circuits 40a and 40b for the respective PO$_2$ and PCO$_2$ standards. Then he enables these reference numbers as by actuating enable 42, which stores these numbers into these memories. They will stay latched-in these memory circuits until the operator again manually intervenes to change the reference numbers, should he for instance use different standards in the measuring chambers.

These memory circuits are furthermore designed for constantly producing at their respective outputs 44a and 44b, a reference signal representative of such reference numbers dialed into these circuits.

These reference signals are also designated with the capital letter B and define one of the inputs to a comparator circuit 50a, 50b and 50c. The other input to this comparator circuit is indicated by the capital letter A and represents the output of the respective channels of the analytical instruments at 104a, 104b and 104c as taken from the respective analog-to-digital converters 100a, 100b and 100c.

The comparator circuits are designed to compare the values as represented by A and B and in instances where A is larger than B, to produce a corresponding output signal on leads 52a, 52b or 52c. If on the other hand, the comparator circuit finds that the signal A is smaller than B, then it will produce an output on leads 54a, 54b or 54c. These respective signals will each connect to AND gates 53 and receive their respective second inputs from a sequencer 272 via lead 274 to enable auto-calibration. Such a sequencer may be designed as more fully described in the above mentioned U.S. Pat. No. 3,672,843.

In instances where the comparator circuit finds that signal A is larger than signal B and upon the receipt of the enable signal via lead 274, the respective AND gate 53 will close switch 55 of an RC sample-and-hold circuit 60a, 60b or 60c so as to charge it up positive. On the other hand, in instances where the comparator circuit finds that signal A is smaller than signal B then in like fashion, the other switch 57 is closed so as to charge the sample-and-hold circuit 60a, 60b or 60c negative through a common respective 58a, or 58b or 58c.

Such an RC sample-and-hold circuit is more fully shown in FIG. 2a. Switches 55 and 57 as well as the third switch indicated as at S3 are preferably each solid state switches and are well-known to those skilled in the art. Switch 55 connects one input of operational amplifier 64 via lead 58 and across resistor R1 to a positive d.c. voltage +0.5v, while switch 57 connects the same input of operational amplifier 64 across resistor R2 to a negative d.c. voltage of −0.5v. The other input of operational amplifier is grounded. It should also be noted that this RC sample-and-hold circuit is powered by internal power supply voltages representing the other two inputs to operational amplifier 64 and that these d.c. voltages are +12v and −12v respectively.

In the feedback loop of this operational amplifier 64 is connected a capacitor marked C1 and in parallel therewith, a resistor R3 and the previously mentioned third switch S3 which is normally open and may be closed by a second reference enable signal coupled thereto via lead 43, as will be more fully described below. The output of the RC sample-and-hold circuit is indicated as at 62 and is across output resistor R4.

The respective values for the operative components of these resistors vary, depending upon in which channel the calibration is being utilized, as more fully given in FIG. 2b.

As may be seen in FIG. 1, the output 62a of the sample-and-hold circuit 60a is coupled to amplifier 13 so as to affect its gain, i.e., "SLOPE" control since this is the $PO_2$ channel. In the other two channels, outputs 62b and 62c of the sample-and-hold circuits 60b and 60c are coupled to amplifiers 23 and 13 respectively and more specifically to their BALANCE, i.e., offset controls.

With particular reference to FIG. 4 of above referred to U.S. Pat. No. 3,642,843, it should be noted that the output 62a of the sample-and-hold circuit 60a would be coupled to SLOPE 114 in the $PO_2$ channel. The output 62b would on the other hand be connected to the lead marked BALANCE 110 therein, while the output 62c would be connected in the pH channel to the lead marked BALANCE 106. Of course, the respective inputs A from the analog-to-digital converters 100a, 100b, 100c to the comparator circuits 50a, 50b, 50c would be derived from the respective digital display means, 100, 102 and 104 as shown in said FIG. 4 of said U.S. Pat. No. 3,764,843.

By way of another example and this time using FIG. I of above referenced U.S. Pat. No. 3,694,734, which of course shows only the $PCO_2$ channel, the instrument output A would be taken from the analog-to-digital converter 100, while the output of the automatic calibration system of the present invention 62b would be coupled to the connection between capacitor 74 and resistor 92 so as to influence the input of operational amplifier 76 in said FIG. 1.

Most common deviations in instrument readings occasioned by small shifts in readings, slow response or system noises will be corrected by the application of the input signals from these RC sample-and-hold circuits coupled, as above described, to their respective channel amplifiers 13, 23 or 33. There may, however, be instances where for one reason or another the error is of such a magnitude as to be beyond the maximum allowed correction range of the sample-and-hold circuit. In such instances the comparator circuit will keep on detecting the differences between signals A and B and produce a further output signal on output leads 56a, 56b or 56c. The signals therefrom are passed through a suitable delay means which may be a one second delay means 66a, 66b or 66c and via an AND gate 68a, 68b or 68c to an error circuit 70a, 70b or 70c. The sequencer 272 at the appropriate time enables these error circuits via lead 276. When that occurs, the particular measuring channel of the instrument will be disabled by suitable means, not shown, well-known to persons skilled in the art. One such means may be that the respective display 102a or 102b or 102c will commence flashing, indicating error and requiring the operator's intervention to correct. Such an error may be occasioned for example by a defective electrode or a broken membrane for such electrode or large and persistent system noise or a rather slow instrument response.

One limitation of the correction range of the sample-and-hold circuits is represented by the internal power supply voltages d.c. +12v and d.c. −12v, driving the sample-and-hold circuit, as shown in FIG. 2A. The second limitation arises from the RC time constant (R1-C1 or R2-C1) of the sample-and-hold circuit and of course from the specific values of these resistors, as shown in FIG. 2b, depending on what channel they happen to be incorporated.

Following a major malfunction in the analytical instrument such as requiring for instance the replacement of a defective electrode, the operator may wish to introduce new reference numbers into the memory circuits 40a, 40b. To do so, he has to adjust the instrument back to zero. This is accomplished by closing switch S3 appearing in the feedback loop of the operational amplifier 64 of the sample-and-hold circuit as shown in FIG. 2a via a signal transmitted over lead 43. At the same time, the memory circuit enable over lead 42 in FIG. 1 will be interrupted. Following correction of the malfunction as by the replacement of the defective electrode, calibration standard is introduced into the measuring chamber in contact with the new electrode and the new reference number from that calibration standard is manually dialed in once again into the respective memory circuit 40a, 40b via leads 41a, 41b. With the new reference numbers in the memory circuit, the same is enabled via lead 42 and at the same time switch S3 is moved to its normally open position.

FIG. 3 depicts the timing diagram of the continuous automatic calibration system of this invention. The uppermost horizontal line represents the value of the reference number B as appearing on output 44a or 44b of the respective memory circuit or as the representative of the constant reference number appearing on lead 44c. Below this and for a shorter period, appears the next horizontal line representative of the instrument's output of a particular measuring channel and shown as A. The distance between these lines is representative of the difference between A and B as they are seen by the particular comparator circuit 50a, 50b or 50c.

Assuming that the instrument has just completed a previous analysis followed by rinsing of the measuring chambers and tubes by flash solution, the instrument automatically introduces respective calibration standards into the measuring chambers, as exemplified by Time I in the drawing in FIG. 3. This is followed by the sequencer 272 allowing a certain time period for the instrument to achieve equilibration with the just introduced calibration standard. This time period is represented by Time II in FIG. 3.

A normally functioning analytical instrument will during this period, adjust the output of its analog-to-digital converter to read exactly the same value as the reference number, thus not requiring any intervention at all by the automatic calibration system of the invention. This is represented by the curve marked "normal response."

Should the measuring channel output A not reach the level of what it should be during this equilibration period for any reason, then at the expiration of this equilibration time period, the sequencer 272 via lead 274, as previously described with reference to FIG. 1, now enables the auto-calibration system of the invention to permit it to attempt instrument readout correction. This auto-calibration occurs during the time period shown as Time III in FIG. 3. If the error to be corrected is within the capability and within the maximum correction range of the sample-and-hold circuit, then the output of the instrument at the respective analog-to-digital converter will once again equal the reference numbers.

In cases, however, where the malfunction is of such magnitude as to be beyond the capability of the system of the invention to correct, the sequencer 272 will then enable the error circuits 70a, 70b, 70c via lead 276 as previously described and keep it enabled during the time period shown as Time IV in FIG. 3. If at this point the instrument signal output A still not equals the reference signal B as seen by the comparator circuit 50a, or 50b or 50c, the signal representative of the difference therebetween will be passed through a suitable delay means such as the one second delay 66a, 66b or 66c and combined with the error enable signal, will actuate the error circuit 70a, 70b, or 70c. This will then start the instrument display 102a, 102b or 102c flashing. Consequently, the operator will be warned of instrument malfunction, requiring his intervention.

Thus I have above described a continuous automatic calibration system and method of an analytical instrument which system is designed to work through constant measurement of a calibration standard and the continuous calibration of instrument, output data to previously dialed in reference numbers. More particularly, the system has been described with reference to a three-channel blood gas instrument. It should be understood that other like analytical instruments may be equally provided with the continuous calibration feature disclosed herein. At the same time, my system also automatically indicates instrument malfunction without requiring any additional specific circuitry. Thus, mu system allows for continuous and automatic corrections of minor system errors caused by transient noises, shifts in reading and slow response, and it will indicate any major instrument malfunction in a manner to warn the operator that his intervention is required.

While a particular embodiment of the invention has been shown and described, various modifications thereof will be apparent to those skilled in the art and therefore it is not intended that the invention be limited to the disclosed embodiment or to details thereof and departures may be made therefrom within the spirit and scope of the invention.

What is claimed is:

1. In an analytical instrument for measuring constituents of a fluid comprising at least one sensor means, first circuitry for producing a signal representative of the constituent sensed by said sensor and including an analog-to-digital converter to allow display of said signal in digital form, the improvement for providing continuous calibration of the instrument by means of a second circuitry comprising a comparator circuit for continuously comparing the output signal of said analog-to-digital converter to a reference signal when calibrating the instruments and for producing an output signal representative of the difference as a result of said comparing, and a sample-and-hold circuit for receiving the output signal of said comparator circuit and for producing in turn a compensatory voltage coupled to said first circuitry.

2. The analytical instrument of claim 1 in which said reference signal is continuously produced by a memory means in response to previously stored reference information therein.

3. The analytical instrument of claim 1 further characterized in having an error display means activated by said comparator circuit when said difference between said instrument output and said reference signal exceeds the maximum allowed correction range of said sample-and-hold circuit as determined by its R-C time constant.

4. The analytical instrument of claim 3 also having a delay means interconnected between said comparator circuit and said error display means.

5. In an analytical instrument for measuring constituents of a fluid comprising at least one sensor means, circuitry for producing a signal representative of the constituent sensed by said sensor and including an analog-to-digital converter to allow display of said signal in digital form, the improvement for providing continuous calibration of the instrument by means of a second circuitry comprising
a memory means for receiving and storing reference information and for producing at its output a reference signal representative of said information,
a comparator circuit having one input for receiving said reference signal and a second input for receiving the output of said analog-to-digital converter when calibrating said instrument and for producing at its output a signal representative of the difference therebetween, a sample-and-hold circuit having an input and an output, with its said input coupled to said comparator circuit output and for producing in response thereto a compensatory voltage at its said output which in turn is coupled to said first circuitry to correct for errors in said signal representative of said constituent.

6. The analytical instrument of claim 5 further characterized in having an error display means coupled via a delay means to the output of said comparator circuit for displaying an error when said difference between the instrument output and said reference signal exceeds the R-C time constant of said sample-and-hold circuit for a period in excess of a pre-determined time.

7. A method of continuously calibrating an analytical instrument useful for measuring constituents of a fluid and having circuitry for producing and displaying a signal representative of such constituents comprising
continuously comparing the output of said instrument to a reference signal when calibrating said instrument,
applying the difference resulting from said comparing to charge or discharge a sample-and-hold circuit, and
coupling the resultant output from said sample-and-hold circuit to said instrument circuitry continuously to adjust its signal output.

8. The method of claim 7 further characterized by constantly measuring calibration standards except when a sample is presented to the instrument for measurement.

9. The method of claim 7 further characterized in that when said difference between instrument output and said reference signal is such as to be beyond the capability of said sample-and-hold circuit to correct,
producing an error signal for warning the operator.

10. The method of claim 9 in which said error signal is produced following the elapse of a pre-determined time period.

11. A method of maintaining an analytical instrument useful for measuring constituents of a fluid and having circuitry for producing and displaying a signal representative of such constituents constantly in stat condition comprising
measuring continuously, except when sampling, calibration standards, comparing continuously, except when sampling, the output of said instrument to a reference signal, applying continuously the difference between said output and said reference signal to charge or discharge a sample-and-hold circuit, coupling continuously, the output of said sample-and-hold circuit to said instrument circuitry continuously to correct its signal display, and producing an error signal for warning the operator when said difference between said output and said reference signal is beyond the capability of said sample-and-hold circuit to correct.

12. The method of claim 11 in which said error signal is produced following the elapse of a pre-determined time period.

13. The method of claim 11 in which said reference signal has been stored in a memory means of said instrument.

* * * * *